United States Patent
Belfort et al.

(10) Patent No.: US 9,055,949 B2
(45) Date of Patent: *Jun. 16, 2015

(54) BALLOON TAMPONADE

(75) Inventors: Michael A. Belfort, Park City, UT (US); Gary A. Dildy, III, Park City, UT (US)

(73) Assignee: B & D MEDICAL DEVELOPMENT, LLC, Park City, UT (US)

( * ) Notice: Subject to any disclaimer, the term of this patent is extended or adjusted under 35 U.S.C. 154(b) by 1055 days.
This patent is subject to a terminal disclaimer.

(21) Appl. No.: 12/069,314

(22) Filed: Feb. 8, 2008

(65) Prior Publication Data
US 2008/0215031 A1 Sep. 4, 2008

Related U.S. Application Data

(60) Provisional application No. 60/900,714, filed on Feb. 9, 2007.

(51) Int. Cl.
*A61M 29/00* (2006.01)
*A61B 17/12* (2006.01)
(Continued)

(52) U.S. Cl.
CPC ..... *A61B 17/12136* (2013.01); *A61B 17/12099* (2013.01); *A61B 17/42* (2013.01); *A61B 2017/00539* (2013.01); *A61B 2017/00557* (2013.01); *A61B 2017/12004* (2013.01)

(58) Field of Classification Search
CPC .................. A61B 2017/12004; A61B 17/42
USPC .......... 606/193, 119, 194, 198, 199; 604/500, 604/37, 97.01, 99.01, 100.01, 101.01, 330
See application file for complete search history.

(56) References Cited

U.S. PATENT DOCUMENTS 2,849,002 A 8/1958 Oddo
3,411,506 A * 11/1968 Velasco ........................ 606/192

(Continued)

FOREIGN PATENT DOCUMENTS

CN 2381340 Y 6/2000
FR 2873014 A 1/2006
(Continued)

OTHER PUBLICATIONS

Barbieri, RL, You Should Add the Bakri Balloon to Your Treatment for OB Bleeds, OBG Management 2009; 21(2):6-10.
(Continued)

*Primary Examiner* — Thomas McEvoy
*Assistant Examiner* — Julie A Szpira
(74) *Attorney, Agent, or Firm* — Winston & Strawn LLP

(57) ABSTRACT

An implantable device is provided for controlling hemorrhage in a body cavity, comprising an expandable balloon and a conduit for supplying a physiologically compatible fluid to inflate the balloon. When the balloon tamponade device is implanted or inserted into the body cavity, it is inflated with a physiologically suitable fluid, so that the balloon generally conforms to the body cavity and exerts compressive force against the walls, tissues or structures of the body cavity to control hemorrhage. The balloon may have a deforming means to limit expansion of the balloon in a direction to facilitate expansion of the balloon in another direction. The device may have additional tubes within the conduit, or a plurality of separate lumens within the conduit or tubes to allow drainage and irrigation to the body cavity. There is also provided a cuff for attachment of an external traction to the balloon tamponade, to facilitate the compressive effect of the device. In a preferred embodiment, there is provided a dual balloon tamponade in which two balloons are axially spaced along the conduit, providing a means to control hemorrhage from two distinct body cavities, such as a uterus and a vagina. There is also provided a method to control hemorrhage in a body cavity by implantation or insertion of the balloon tamponade, inflating the balloon with a fluid to a sufficient pressure and retaining the fluid pressure within the balloon for a sufficient period of time to determine whether hemorrhage has been controlled. A kit comprising the balloon tamponade apparatus is also provided.

30 Claims, 6 Drawing Sheets

(51) Int. Cl.
*A61B 17/42* (2006.01)
*A61B 17/00* (2006.01)

(56) References Cited

U.S. PATENT DOCUMENTS

| | | | |
|---|---|---|---|
| 3,848,602 A | 11/1974 | Gutnick | |
| 3,848,603 A | 11/1974 | Throner | |
| 3,875,939 A | 4/1975 | Bolduc | |
| 4,005,709 A | 2/1977 | Laerdal | |
| RE29,207 E | 5/1977 | Bolduc | |
| 4,207,891 A | 6/1980 | Bolduc | |
| 4,224,945 A | 9/1980 | Cohen | |
| 4,270,541 A | 6/1981 | Okamoto | |
| 4,404,971 A | 9/1983 | LeVeen | |
| 4,445,892 A | 5/1984 | Hussein | |
| 4,464,175 A | 8/1984 | Altman | |
| 4,552,557 A | 11/1985 | Rangaswamy | |
| 4,619,261 A | 10/1986 | Guerriero | |
| 4,693,704 A | 9/1987 | Ogita | |
| 4,848,344 A | 7/1989 | Sos | |
| 4,976,692 A | 12/1990 | Atad | |
| 4,997,438 A | 3/1991 | Nippepr | |
| 5,062,425 A | 11/1991 | Tucker | |
| 5,234,459 A | 8/1993 | Lee | |
| 5,248,304 A | 9/1993 | Vigdorchik | |
| 5,308,326 A | 5/1994 | Zimmon | |
| 5,338,297 A | 8/1994 | Kocur | |
| 5,391,179 A | 2/1995 | Mezzoli | |
| 5,571,153 A | 11/1996 | Wallsten | |
| 5,613,950 A | 3/1997 | Yoon | |
| 5,624,399 A * | 4/1997 | Ackerman | 604/103.03 |
| 5,626,601 A * | 5/1997 | Gershony et al. | 606/194 |
| 5,643,315 A | 7/1997 | Daneshvar | |
| 5,674,239 A | 10/1997 | Zadini | |
| 5,709,657 A | 1/1998 | Zimmon | |
| 5,743,852 A * | 4/1998 | Johnson | 600/207 |
| 5,749,845 A | 5/1998 | Hildebrand | |
| 5,782,856 A | 7/1998 | Flores-Valderrama de Gonzalez | |
| 5,814,016 A | 9/1998 | Valley | |
| 5,935,098 A | 8/1999 | Blaisdell | |
| 5,947,991 A | 9/1999 | Cowan | |
| 5,957,962 A * | 9/1999 | Wallsten et al. | 607/104 |
| 6,024,753 A | 2/2000 | Claren | |
| 6,206,868 B1 | 3/2001 | Parodi | |
| 6,234,958 B1 | 5/2001 | Snoke | |
| 6,395,012 B1 * | 5/2002 | Yoon et al. | 606/193 |
| 6,460,541 B1 | 10/2002 | Shah | |
| 6,511,469 B2 | 1/2003 | Ackerman | |
| 6,520,977 B2 | 2/2003 | Piraka | |
| 6,648,842 B2 | 11/2003 | Horkel | |
| 6,656,141 B1 | 12/2003 | Reid | |
| 6,676,680 B1 * | 1/2004 | Packer | 606/193 |
| 6,796,993 B2 | 9/2004 | Lambroza | |
| 6,884,254 B2 | 4/2005 | Brooks | |
| 6,951,569 B2 | 10/2005 | Nohilly | |
| 6,958,052 B1 | 10/2005 | Charlton | |
| 6,981,981 B2 | 1/2006 | Reiley | |
| 7,004,963 B2 | 2/2006 | Wang | |
| 7,018,392 B2 | 3/2006 | Hudson | |
| 7,108,706 B2 | 9/2006 | Hogle | |
| 7,156,860 B2 | 1/2007 | Wallsten | |
| 7,156,861 B2 | 1/2007 | Scribner | |
| 7,172,586 B1 * | 2/2007 | Dae et al. | 604/500 |
| 7,179,251 B2 | 2/2007 | Palasis | |
| 7,220,252 B2 | 5/2007 | Shah | |
| 7,311,717 B2 | 12/2007 | Egle | |
| 7,498,477 B2 | 3/2009 | Wada | |
| 7,540,876 B2 * | 6/2009 | Connors et al. | 606/194 |
| 7,935,077 B2 * | 5/2011 | Thor et al. | 604/67 |
| 2001/0041896 A1 | 11/2001 | Reiley | |
| 2002/0151880 A1 | 10/2002 | Lafontaine | |
| 2003/0114878 A1 | 6/2003 | Diederich | |
| 2003/0212426 A1 | 11/2003 | Olsen | |
| 2004/0030352 A1 | 2/2004 | McGloughlin | |
| 2004/0116955 A1 * | 6/2004 | Foltz et al. | 606/193 |
| 2004/0220610 A1 | 11/2004 | Kreidler | |
| 2005/0015047 A1 * | 1/2005 | Shah | 604/101.02 |
| 2005/0049627 A1 | 3/2005 | Claren | |
| 2005/0149100 A1 | 7/2005 | Foltz | |
| 2005/0226855 A1 * | 10/2005 | Alt et al. | 424/93.7 |
| 2005/0267509 A1 | 12/2005 | Davis, Jr. | |
| 2005/0277906 A1 * | 12/2005 | Brugger et al. | 604/411 |
| 2006/0058831 A1 * | 3/2006 | Atad | 606/193 |
| 2006/0089658 A1 | 4/2006 | Harrington | |
| 2006/0095066 A1 * | 5/2006 | Chang et al. | 606/199 |
| 2006/0173486 A1 * | 8/2006 | Burke et al. | 606/193 |
| 2006/0178692 A1 | 8/2006 | Condrea | |
| 2006/0211973 A1 | 9/2006 | Gregory | |
| 2006/0212064 A1 | 9/2006 | Shah | |
| 2006/0235461 A1 | 10/2006 | Harter | |
| 2006/0271092 A1 | 11/2006 | Reed | |
| 2007/0066990 A1 * | 3/2007 | Marsella et al. | 606/193 |
| 2007/0191881 A1 | 8/2007 | Amisar | |
| 2007/0239110 A1 | 10/2007 | Shah | |
| 2008/0027421 A1 | 1/2008 | Vancelette | |
| 2008/0243103 A1 | 10/2008 | Whetham | |
| 2009/0093758 A1 | 4/2009 | Gross | |
| 2009/0099515 A1 | 4/2009 | Quilter | |
| 2009/0204099 A1 | 8/2009 | Feloney | |

FOREIGN PATENT DOCUMENTS

| | | |
|---|---|---|
| GB | 10340788 A | 1/1974 |
| GB | 003372 A | 2/2005 |
| WO | 8501212 A1 | 3/1985 |
| WO | 0050114 A1 | 8/2000 |
| WO | 0172221 A1 | 10/2001 |
| WO | 2005013834 A1 | 2/2005 |
| WO | 2005030064 A1 | 4/2005 |
| WO | 2008046050 A2 | 4/2008 |
| WO | WO-2008100433 A2 | 8/2008 |

OTHER PUBLICATIONS

Barbieri, RL, Planning Reduces the Risk of Maternal Death: This Tool Helps, OBG Management 2009; 21(8):8-10b.
Barbieri, RL, Massive Obstetric Hemorrhage: High- and Low-tech Tools, OBG Management 2005; 17(12):9-10.
Zemlyn, S, The Length of the Uterine Cervix and its Significance, J Clin. Ultrasound 1981; 9:267-69.
Rogers, M, Postpartum Hemorrhage and Other Problems of the Third Stage, Ch. 77 pp. 1559-1579 in: High Risk Pregancy (editors James DK, WeinerCP, Steer PJ, Gonik B, 3rd Ed., Elsevier 2006).
Anthony, J, Major Obstetric Hemorrhage and Disseminated Intravascular Coagulation, Ch. 79 pp. 1606-1623 in: High Risk Pregnancy (editors James DK, Weiner CP, Steer PJ, Gonik B, 3rd Ed., Elsevier 2006).
Jones, Howard W., Hysterectomy, Ch 31 pp. 799-828 in: TE Linde'S Operative Gynecology (editors Rock JA and Jones HW, 9th Ed., Lippincott, Williams & Wilkins 2003).
Parker, Lynn, Gynecologic Surgery for Obstetric Patients, Ch 32 pp. 829-863 in: TE Linde's Operative Gynecology ( editors Rock JA and Jones HW, 9th Ed., Lippincott, Williams & Wilkins 2003).
Jackobovitz, A, Postpartum Hemorrhage, Ch. 22 pp. 261-280 in: Operative Obstetrics (editors Apuzzio J, Vintzileos A and Iffy L, 3rd Ed., Taylor & Francis 2006).
Stitley, ML, Postpartum Hemorrhage Solution to 2 Intractable Cases, OBG Management (2007); 19(4):64-76.
Danso, D, Internal Uterine Tamponade, Ch. 28 pp. 263-267 in: A Textbook of Postpartum Hemorrhage a Comprehensive Guide to Evluation, Management and Surgical Intervention (editors B-Lynch, E, Keith, LG, Lalonde, AB and Karoshi, M, Sapiens UK 2006).
Ferrazzani, S, The Balloon Internal Uterined Tamponade as a Diagnostic Test, Ch. 29 pp. 268-276 in: A Textbook of Postpartum Hemorrhage a Comprehensive Guide to Evluation, Management and Surgical Intervention (editors B-Lynch, E, Keith, LG, Lalonde, AB and Karoshi, M, Sapiens UK 2006).
Clinical Innovations, ClearView Uterine Manipulator (Brochure).
Clinical Innovations, Koala IUPC (webpage).
PNN Medical, Caveterm System (webpage).

(56) References Cited

OTHER PUBLICATIONS

Univ. of Michigan, Med., Management of Postpartum Hemorrhage with the SOS Bakri Balloon Tamponade Catheter.
Condus, GS, The "Tamponade Test" in the Management of Severe Postpartum Hemorrhage, Obstet. & Gynecol. 2003; 101(4):767-72.
Lau, M S K, Use of a Large Rusch Hydrostatic Catheter Balloon to Control Postpartum Haemorrhage Resulting from a Low Placental Implantation, Singapore Med J 2009; 50(9):e321-23.
International Patent Application Serial No. PCT/US2008/001708, International Search Report and Written Opinion, mailed Aug. 4, 2009.
Abu-Rustum, RS, Inner Myometrial Laceration Causing a Massive Postpartum Hemorrhage, J. Reproductive Med. 2006; 51:135-137.
ACOG Clinical Review May-Jun. 2009, p. 3, Synopsis and Commentary on Uterine Balloon Tamponade for Postpartum Hemorrhage (article by Doumouchtsis SK, Acta Obstet Gynecol Scand. 2008; 87:849-855).
Bagga, R, Uterovaginal Packing with Rolled Gauze in Postpartum Hemorrhage, Medscape General Med. 2004; 6(1):50.
Bakri, YN, Placenta Percreta with Bladder Invasion: Report of Three Cases, Am. J. Perinatology 1993;10(6):463-470.
Bakri, YN, Uterine Tamponade Drain for Hemorrhage Secondary to Placeta Previa-Accreta, Int. J. Gynecol. Obstet.1992; 37:302.
Bakri, YN, Tamponade Balloon for Obstetrical Hemorrhage, Int. J. Obstet. & Gynecol. 2001; 74:139-142.
Barnhardt, KT, Baseline Dimensions of the Human Vagina, Human Reproduction 2006; 21(6):1618-1622.
Baskett, TF, Surgical Management of Severe Obstetric Hemorrhage: Experience with an Obstetric Hemorrhage Equipment Tray, J. Obstet. Gynaecol. Can. 2004; 26(9):805-505.
Bowen, LW, Use of a Large Foley Catheter Balloon to Control Postpartum Hemorrhage Resulting from a Low Placental Implantation, J. Reproductive Med. 1985; 38(8):623-625.
Cirese, E, Emergency Pelvic Packing to Control Intraoperative Bleeding After a Piver Type-3 Procedure. An Unusual Way to Control Gynaecological Hemorrhage, Euro. J. Gynaecol. Oncol. 2003;XXIV(1):99-100.
Cho, Y, Ultrasonic Visualization of Balloon Placement for Uterine Tamponade in Massive Primary Postpartum Hemorrhage, Ultrasound Obstet. Gynec. 2008; 32-711-713.
Clark, SL, Maternal Death in the 21st Century: Causes, Prevention, and Relation to Cesarean Delivery, Am. J. Obstet. & Gynecol. 2008; 199:36.e1-36.e5.
Dabelea, V, Intrauterine Balloon Tamponade in the Management of Postpartum Hemorrhage, Am. J. Perinatol. 2007; 24:359-364.
Digiacomo, C, Practice Management Guidelines for Hemorrhage in Pelvic Fracture, The EAST Practice Management Guidelines Work Group, 2001.
Dildy, GA, An Effective Pressure Pack for Severe Pelvic Hemorrhage, Obstet. & Gynecol. 2006; 108(5):1222-1226.
Doumouchtsis, SK, Management of Postpartum Hemorrhage by Uterine Balloon Tamponade: A Prospective Evaluation of Effectiveness, Acta Obstet. et Gynecol. Scand. 2008; 87(8):849-855.
Druzin, ML, Packing of Lower Uterine Segment for Control of Post Cesarean Bleeding in Instance of Placenta Previa, Surgery Gynecol. & Obstet. 1989; 169:543-545.
El Hennewy, M, Uterine and Vaginal Balloons for Control of Massive PPH, www.obgyn.net.
Farag, EE, Surgical Packing as a Means of Controlling Massive Haemorrhage in Association with Advanced Abdominal Pregnancy, Euro. J. Obstet. & Gynecol. and Reproductive Biology 2003; 109:106-107.
Francois, KE, Antepartum and Postpartum Hemorrhage, Ch. 18, Gabbe: Obstetrics: Normal and Problem Pregnancies (5th Ed.) 2007.
Garagiola, DM, Anatomic Changes in the Pelvis after Uncomplicated Vaginal Delivery: A CT Study on 14 Women, Am. J. Roentgen. 1989; 153:1239-1241.
Hsu, S, Use of Packing in Obstetric Hemorrhage of Uterine Origin, J. Reproductive Med. 2003; 48(2):69-71.
Holub, Z, Laparoscopic Management of Bleeding after Laparoscopic of Vaginal Hysterectomy, J. Soc. Laparascopic Surgeons 2004; 8:235-238.
Johanson, R, Management of Massive Postpartum Hemorrhage: Use of a Hydrostatic Balloon Catheter to Avoid Laparotomy, 2001; 108:420-422.
Johns Hopkins Hospital, Dept. OBGYN, SOS Bakri Balloon Tamponade Catheter, pp. 1-21 (Sep. 2005).
Keller, TM, Obstetric MR Pelvimetry:Reference Values and Evaluation of Inter-and Intraobserver Error and Intraindividual Variability, Radiology 2003; 227(1):37-43.
Kilpatrick, S, Normal Labor and Delivery, Ch. 12 in Gabbe: Obstetrics: Normal and Problem Pregnancies (editors Gabbe S, Niebyl J, Simpson JL, Galen H, Goetzl L, Jauniaux ERM, Landon M, 5th Ed., Elsevier 2007.
Kolomeyevskaya, NV, Balloon Tamponade of Hemorrhage after Uterine Curretage for Gestational Trophoblastic Disease, Obstet. & Gynecol. 2009; 113(2):557-560.
Li, Y-T, A Useful Technique for Control of Severe Cesarean Hemorrhage: Report of Three Cases, Chang Gung Med. J. 2002; 25:548-552.
Langlois, PL, The Size of the Normal Uterus, J. Reproductive Med. 1970; IV(6):220-228.
Madden, T, Successful Management of Second-Trimester Post Abortion Hemorrhage with an Intrauterine Balloon Tamponade, Obstet. & Gynecol. 2009;113(2):501-503.
Maier, RC, Control of Postpartum Hemorrhage with Uterine Packing, Am. J. Obstet. Gynecol. 1993; 169:317-323.
Naqvi, S, Conservative Management of Primary Postpartum Hemorrhage, JCPSP 2004; 14(5):296-297.
Nwagha, UI, Intraoperative Uterine Packing with Mops: An Effective, but Underutilized Method of Controlling Postpartum Haemorrhage-Experience from South Eastern Nigeria, Nigerian J. Med. 2005; 14(3):279-282.
Parulekar, SV, Post-hysterectomy Broad Ligament Haematoma: A Complication of Vaginal Packing, J. Postgraduate Med. 1989; 35(1):51-53.
Shah, T, Polyurethane Thin-Film Welding for Medical Device Applications, Medical Device and Design Industry, Sep. 2002.
Polyzen, Inc., Proprietary New Polyurethane Film Weld Seal System Makes an Invisible Seal as Strong as the Material Itself.
Polyzen, Inc., Thermoformed Polyurethane Film Process Breakthrough Allows Polyzen to Weld Low Pressure Balloons with Rations of 1 to 20.
Rameswak, S, Gauze Packing for Aspirin-Induced Hemorrhage in Vaginal Hysterectomy, Int. Urogynecol. J. 2004; 15:59-60.
Reed, BD, Postpartum Hemorrhage, Am. Family Physician 1998; 37(3):112-120.
Tattersal, M, Balloon Tamponade for Vaginal Lacerations Causing Severe Postpartum Hemorrhage, B. J. Obstet. Gynecol. 2007; 114:647-648.
Utah Medical Products, Inc., BT-Cath Balloon Tamponade Catheter for Postpartum Hemorrhage, Instructions for Use.
Utah Medical Products, Inc., BT-Cath webpage, www.utahmed.com/btcath.htm.
Utah Medical Products, Inc., BT-Cath Uterine Balloon Tamponade Catheter for Postpartum Hemorrhage, Brochure.
Utah Medicalproducts, Inc., BT-Cath Balloon Tamponade Catheter for PPH or Intrauterine Bleeding Post D&C.
Cook Medical, Bakri Postpartum Balloon, The simple solution for postpartum hemorrhage, pp. 1-49 (2008).
Cook, Bakri Postpartum Balloon (Instructions for Use).
Cook Medical, Bakri Postpartum Balloon, A Simple Solution for Postpartum Hemorrhage, pp. 1-4 (2008).
Cook Medical, Uterine Balloon Stent (webpage).
Cook OB/GYB, SOS Bakri Tamponade Balloon Catheter, The Simple Solution for Postpartum Hemorrhage, pp. 1-32 (2004).
"Canadian Application Serial No. 2,677,738, Voluntary Amendment filed Aug. 19, 2010", 8 pgs.
"Chinese Application Serial No. 200880010540.0, Office Action mailed Aug. 3, 2011", 6 pgs.
"Chinese Application Serial No. 200880010540.0, Response filed Feb. 17, 2012 to Office Action mailed Aug. 3, 2011", 9 pgs.

(56) References Cited

OTHER PUBLICATIONS

"International Application Serial No. PCT/US2008/001708, International Preliminary Report on Patentability mailed Aug. 19, 2009", 13 pgs.
"International Application Serial No. PCT/US2008/001708, International Search Report mailed Aug. 4, 2009", 8 pgs.
"International Application Serial No. PCT/US2008/001708, International Written Opinion mailed Aug. 14, 2009", 12 pgs.
"Australian Application Serial No. 2008216866, Examiner Report mailed Jul. 2, 2012", 3 pgs.
"Chinese Application Serial No. 200880010540.0, Office Action mailed Jun. 28, 2012", With English Translation, 14 pgs.
"Chinese Application Serial No. 200880010540.0, Response filed Oct. 15, 2012 to Office Action mailed Jun. 28, 2012", CN Response Only, 5 pgs.
"European Application Serial No. 08725353.0, Office Action mailed Aug. 14, 2012", 5 pgs.
"Australian Application Serial No. 2008216866, Request to Amend filed Jan. 29, 2014 in response to Examiner Report mailed Jul. 2, 2012", 24 pgs.
"Chinese Application Serial No. 200880010540.0, Decision on Rejection mailed Jan. 23, 2013", (w/ English Translation), 10 pgs.
"Chinese Application Serial No. 200880010540.0, Request for Reexamination filed May 7, 2013 in response to Decision on Rejection mailed Jan. 23, 2013", (w/ English Translation of Amended Claims), 10 pgs.
"European Application Serial No. 08725353.0, Response filed Feb. 22, 2013 to Office Action mailed Aug. 14, 2012", 26 pgs.
Gary A. Dildy et al., "Initial Experience With a Dual-Balloon Catheter for the Management of Postpartum Hemorrhage", Research Obstetrics, American Journal of Obstetrics & Gynecology, vol. 210, No. 2, pp. 136-138, Feb. 2014.

* cited by examiner

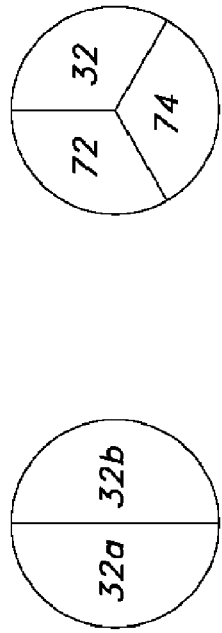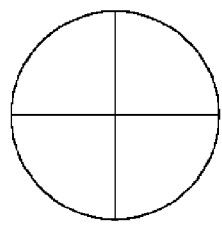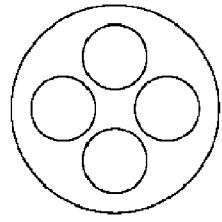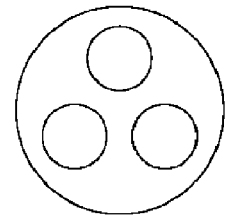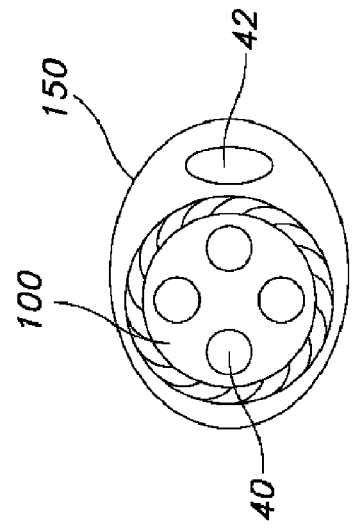

BALLOON TAMPONADE

CROSS-REFERENCE TO RELATED APPLICATIONS

The application claims the benefit of priority under 35 U.S.C. §119(e) of provisional U.S. Patent Application No. 60/900,714, filed Feb. 9, 2007, which application is incorporated herein by this reference.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

The present invention relates generally to the field of medicine and, more particularly, to a balloon tamponade device and methods for controlling hemorrhage in a body cavity.

2. Related Art

The pelvis is the bony structure located at the base of the spine. Each hipbone (os coxae) consists of three bones: the illium, ischium, and the pubis. The two hipbones are joined anteriorly at the symphysis pubis and posteriorly to the sacrum. The pelvis incorporates the socket portion of the hip joint for each leg and forms the lower limb girdle of the skeleton. The pelvic cavity is a body cavity that is bounded by the bones of the pelvis and which primarily contains the reproductive organs, the urinary bladder, the appendix, part of the large intestine and the rectum. The abdominal cavity contains the stomach, spleen, liver, gall bladder, pancreas, small intestine and part of the large intestine. The abdominal cavity is not physically separated from the pelvic cavity, and frequently the cavities are referred to collectively as the abdominopelvic cavity.

Loss of blood internally into the abdominopelvic cavity occurs frequently with blunt trauma, blast injuries, pelvic fractures and abdominal or pelvic surgeries (e.g. hysterectomy), that cause injury to the network of blood vessels lying on the inner wall of the abdominal cavity and/or pelvic cavity. Up to 52% of patients with pelvic fractures will develop hemorrhagic shock in the emergency department. The management of abdominal and pelvic hemorrhage has been limited to more rigorous interventions, including pharmaceutical (e.g., recombinant Factor VIIa), surgical (e.g., vascular ligation, such as hypogastric artery ligation) and radiological (e.g., selective arterial embolization). Packing of the pelvic cavity (e.g., Logothetopulos, mushroom or umbrella pack) has been used to control pelvic hemorrhage, but there is not commercially available product. Pelvic packing is performed by the physician in situ using a sterile bag (e.g., a trash bag, X-ray cassette drape, etc) that is packed with gauze or other packing material that may later be removed from the bag. See, Dildly et al., *An Effective Pressure Pack for Severe Pelvic Hemorrhage*, Obstet. & Gynecol. 108(5):1222-1226 (2006). However, pelvic packing is difficult to insert, may not provide pressure where most needed (at the specific site of bleed or near involved vasculature), and may mask continued bleeding, making it difficult to determine whether hemorrhage has been effectively managed by the pelvic pack.

Significant blood loss may also occur in gynecologic and obstetric patients, for example due to trauma, abortion procedures, vaginal or cesarean delivery (e.g., lacerations to uterus, vagina or broad ligament or retained placental tissue), or due to a variety of other causes, including, placental abruption, placenta previa, placenta accreta or placenta percret or placenta increta, uterine atony, uterine inversion, coagulation disorders, chronic enodmetritis and placental polyps. Treatments to manage gynecologic/obstetric hemorrhage include: blood product (e.g., blood or platelet transfusion) and/or pharmaceutical intervention (e.g., Factor VIIa or other clotting mediators, and uterotonics, such as oxytocin, prostaglandins, misoprostol, methylergonovine, carboprost tromethamine, dinoprostone), uterine massage and compression sutures, surgical procedures (e.g., vascular ligation of the iliac, hypogastric, uterine and/or ovarian arteries), and interventional radiology procedures (e.g., selective arterial embolization). Hysterectomy is the measure of last recourse, particularly if the patient is of low parity.

Uterine and vaginal packing, similar to pelvic packing, have been used to treat uterine and vaginal hemorrhage, but packing for gynecologic/obstetric hemorrhage has largely been replaced by use of balloon catheters that were originally developed for other purposes, such as Foley catheters, Rusch catheters and Sengstaken-Blakemore tubes. See, Bowen L W and Beeson, J H, *Use of a Large Foley Catheter Balloon to Control Postpartum Hemorrhage Resulting from a Low Placental Implantation*, J. Reprod. Med. 30:623-628 (1985); Condous, G S et al., *The Tamponade Test in the Management of Massive Postpartum Hemorrhage*, Obstet. and Gynecol. 1201 (4):767-772 (2003). The SOS Bakri Tamponade Balloon Catheter (manufactured by Cook Medical Inc., Bloomington, Ind.) is the only commercially available balloon catheter specifically developed for management of postpartum hemorrhage from an intact uterus. Bakri Y N, *Uterine tamponade-drain for hemorrhage secondary to placenta reviaaccreta*, Int. J. Gynecol Obstet 27: 302-303 (1992), Bakri, Y N, *Balloon device for control of obstetrical bleeding*, Euro J. Obstet Gynecol. Reprod. Biol. 86:584 (1999); Bakri Y N, et al., *Tamponade-balloon for obstetrical bleeding*, Int. J. Gynecol. Obstet. 74: 139-142 (2001). Balloon tamponade devices to manage vaginal and uterine hemorrhage are disclosed in U.S. Pat. Nos. 4,552,557; 5,062,425; 5,571,153; 5,674,239; 6,024,753; 6,520,977; 6,676,680; 7,220,252; and U.S. Patent Application Pub. Nos. 2006/0173486, 2005/0049627, and 2004/0030352.

However, there are disadvantages in existing balloon catheters used for uterine or vaginal hemorrhage. Existing balloon catheters are of a small volume (maximum full of 500 milliliters or less), and cannot be rapidly filled (inflated with a fluid) because the elasticity of the balloon creates a counter-inflation pressure that must first be overcome. For example, it takes significant applied pressure to inflate a Bakri device, delaying full inflation time (the inflation necessary to exert compression) for three-minutes or more. Also, when these balloon catheter devices are used to control uterine hemorrhage, external traction is applied to the lower portion of the balloon device so that it properly sits at the base of the lower uterine segment. Traction to the balloon tamponade requires a means to prevent the balloon catheter from being pulled downward into the vagina. Typically, the vagina is separately packed (even if not bleeding) to prevent the uterine balloon tamponade from being pulled by traction into the vagina, resulting in yet additional delay and preventing rapid control of uterine hemorrhage. Furthermore, frequently it is desirable to simultaneously control hemorrhage in the uterus and vagina, but there is no unitary device to provide tamponade to both such body cavities.

Due to the substantially larger volume of the abdominopelvic cavity, none of these existing vaginal or uterine balloon catheter devices is suitable for controlling hemorrhage in the pelvic or abdominal cavity. Thus, there is a need for an effective means to control hemorrhage from an abdominal or pelvic cavity. There is also a need to control hemorrhage from an abdominal or pelvic cavity that does not mask a continuing bleed. Further, there is a need for a device to control hemorrhage that provides separate lumens for administering fluids to the body cavity and for draining body fluids and debris from the body cavity. Further, there is a need for an apparatus having the ability to simultaneously control hemorrhage from a uterus and a vaginal body cavity. There is also a need for an effective means to rapidly control hemorrhage in a body cavity.

The present invention is directed to overcoming one or more of the problems set forth above. The inventions described herein are not limited in any manner by the descriptions or definitions, or the diagnostic or clinical indications or uses described herein.

SUMMARY OF THE INVENTION

The present invention relates to an apparatus (sometimes referred to herein as a "balloon tamponade") to control hemorrhage in a body cavity, and unless otherwise provided herein, "body cavity" shall mean a pelvic cavity, abdominal cavity, a uterus or a vagina. After the apparatus is implanted or inserted into a pelvic cavity or abdominal cavity the balloon is inflated to expand the balloon to a shape within the body cavity. Expansion of the balloon so that it generally conforms as closely as possible to the shape of the body cavity, causes a compressive force or pressure against a wall, tissue, structure or a site that is bleeding and thereby controls hemorrhage from the body cavity. The apparatus of the present invention may also be used as a prophylactic device in patients who may be expected to experience internal hemorrhage in a body cavity (e.g., due to trauma or surgery or other medical condition), such that the device is implanted before hemorrhage begins and may prevent hemorrhage or limit the severity of hemorrhage that does occur.

Specifically, in one aspect of the invention there is provided an expansible, deformable material (referred to herein as a "balloon") and a conduit, the balloon sealaby surrounding at least a portion of the conduit. The conduit has a first lumen (a first inflation lumen) in fluid communication with the interior of the balloon to provide a channel to inflate the balloon when it is implanted in a body cavity. The conduit is further comprised of a second lumen and a deforming means to deform the shape of the balloon so that a balloon dimension is changed in an axis or a direction. Deformation of the balloon changes the dimension of the balloon in first direction or axis causing expansion and compressive forces to be directed in a preferred second direction or axis. For example, deforming the balloon at the dome changes the shape from an ellipse in the longitudinal axis to an ellipse in the lateral axis, thereby directing expansion more laterally in the posterior/anterior axis, against the sides of the body cavity.

In yet other preferred embodiments, the conduit of the pelvic balloon tamponade extends the length of the balloon and is sealably surrounded by the balloon at the distal and proximal ends of the balloon. The conduit comprises an inflation lumen and a second irrigation/drainage lumen. The irrigation/drainage lumen has a distal end and a proximal end and lumen openings at or near the opposing distal and proximal ends of the conduit, in communication with the pelvic or abdominal cavity and the exterior of the subject's body, to deliver fluids to (irrigate) and/or receive fluids and debris from (drain) the pelvic or abdominal cavity. In yet another aspect, the tube may have separate irrigation and drainage lumens to minimize contamination of the body cavity that may occur when irrigation and drainage is accomplished through the same lumen. In still other embodiments, separate inflation lumens and deflation lumens may be provided, each lumen being in communication with the balloon interior, to permit circulation or replacement of the inflation media while maintaining substantially continuous pressure within the balloon interior, which is preferred when warming or cooling of the body cavity is desired.

In yet another embodiment, the balloon apparatus provides a means to control hemorrhage from separated areas within the body cavity or from a body cavity and a natural or created lumen or orifice in the body (e.g., a pelvic cavity and a vagina, or a pelvic cavity and an orifice created in a perineum). In a preferred embodiment, the balloon apparatus comprises at least two balloons axially spaced along the inflation tube, each balloon capable of being inflated to control hemorrhage from the separate areas. In other preferred embodiments, separate inflation lumens are provided so that the balloons may be separately and differentially inflated, or such that only one of such balloons may be inflated.

In other embodiments, the balloon apparatus may further comprise an introducer or guide to assist insertion and placement of the balloon apparatus when inserted through a lumen or channel in a subject (e.g., insertion through the vagina of a female subject who has had a hysterectomy or insertion through an opening created in the perineum of a male subject). In yet other embodiments, a rigid or semi-rigid collar located at the base of the balloon is provided to secure a traction means to the apparatus, thereby preventing displacement of the balloon apparatus or upward movement of the balloon apparatus further into the body cavity. In still other embodiments, the balloon apparatus may further comprise one or more connecting means (such as fittings, luers/leurs, adapters, etc.) to connect a lumen of a tube or conduit of the balloon apparatus to tubing and/or to an inflation media source that is external to the body. In still other embodiments, the balloon apparatus may further comprise a control means to retain the inflation medium within the balloon. Control means (e.g, valves, stop-cocks, clamps) may also be provided to seal and unseal a lumen of a tube or to control influx or efflux through the lumen of tubing, tubes or conduits of various embodiments of the invention. In still other embodiments, the balloon apparatus may further comprise a pressure detection means, such as a pressure gauge, to detect the internal pressure of the media within the balloon.

In yet another aspect of the invention, there is provided a method of controlling hemorrhage from a pelvic or abdominal cavity by inserting or implanting an expansible balloon into a pelvic or abdominal cavity of a subject that is experiencing (or may be expected to experience) hemorrhage. Once implanted, the balloon is inflated with a biologically and physiologically compatible fluid, and is retained in its inflated state within the body cavity at a pressure and for a period of time, as may be determined by clinical judgment to be sufficient to control hemorrhage. Preferably, the inflation pressure (internal pressure) of the balloon would be maintained at or just above the blood pressure of the subject. The inflated balloon apparatus may be retained in the subject for any suitable period of time, in most instances from approximately 20 minutes to 72 hours, and preferably only as long as is necessary to determine that hemorrhage has been effectively controlled (evidence of clotting, no further bleeding from the body cavity, or other sign of hemostasis), or that damage is so severe that the balloon apparatus cannot adequately manage hemorrhage such that more significant intervention is required (e.g., surgical or radiological intervention). Medical personnel may assess whether hemorrhage has been controlled or staunched by release of the inflation medium from the balloon (by suction or release or opening of a control means)

In still another aspect, the invention provides a balloon tamponade kit, comprising a balloon apparatus, one or more inflation supply tubes, a drainage effluent tubes, a fluid collection means and instructions for use and implantation of the device.

Further aspects, features, embodiments and advantages of the invention will be apparent from the following disclosure, the claims and the drawings.

BRIEF DESCRIPTION OF THE DRAWINGS

The invention will be better understood and further features, details and advantages of the invention will appear more clearly with reference to the diagrammatic drawings, illustrating specific embodiments of the invention by way of non-limiting example only:

FIGS. 6a, 6b, 6c, 6d, 6e, 6f, and 6g illustrate cross-sectional views of conduits having configurations of lumens suitable for various embodiments of the invention.

DESCRIPTION OF THE INVENTION

The following description includes a description of the best mode or modes of the invention as presently known. The descriptions are not intended to in any way limit the invention and are examples given only for illustration, so that by reference to the accompanying drawings one skilled in the art may appreciate the features, aspects, and advantages of the invention.

The present invention for controlling hemorrhage in a pelvic or abdominal cavity of a subject comprises an expansible material (e.g., a balloon) that is implanted in the body cavity and, when inflated by a fluid medium, generally conforms to the shape of the body cavity, exerting a compressive force against at least one wall, surface, structure or site (e.g., a bone, a blood vessel, an organ or a tissue) to control hemorrhage from the body cavity. The various embodiments of the apparatus disclosed herein are sometimes referred to herein as a "balloon tamponade" and/or "balloon apparatus."

When used herein in reference to a balloon of the present invention, the following terms shall have the following meaning: "deflated" shall mean a condition of the balloon immediately prior to and upon after insertion, followed by "fill", which indicates that the balloon has been inflated, then followed by drain in which the inflating fluid is released so that the balloon returns to the deflated state (e.g., the condition of the balloon prior to removal under intended use conditions); "deform" shall mean a feature or attribute of a balloon that allows the shape of the balloon to be changed when desired; "conform" shall mean a condition of a balloon wherein the balloon has changed shape to substantially mirror that of the implantation site; "compliance" shall mean a feature or attribute of a balloon that allows the balloon to change shape to substantially mirror that of the implantation site in response to a resistance force within the body cavity (e.g., due to encountering a wall, structure or tissue or organ) or in response to a traction or other force applied to the balloon.

Figure 1:
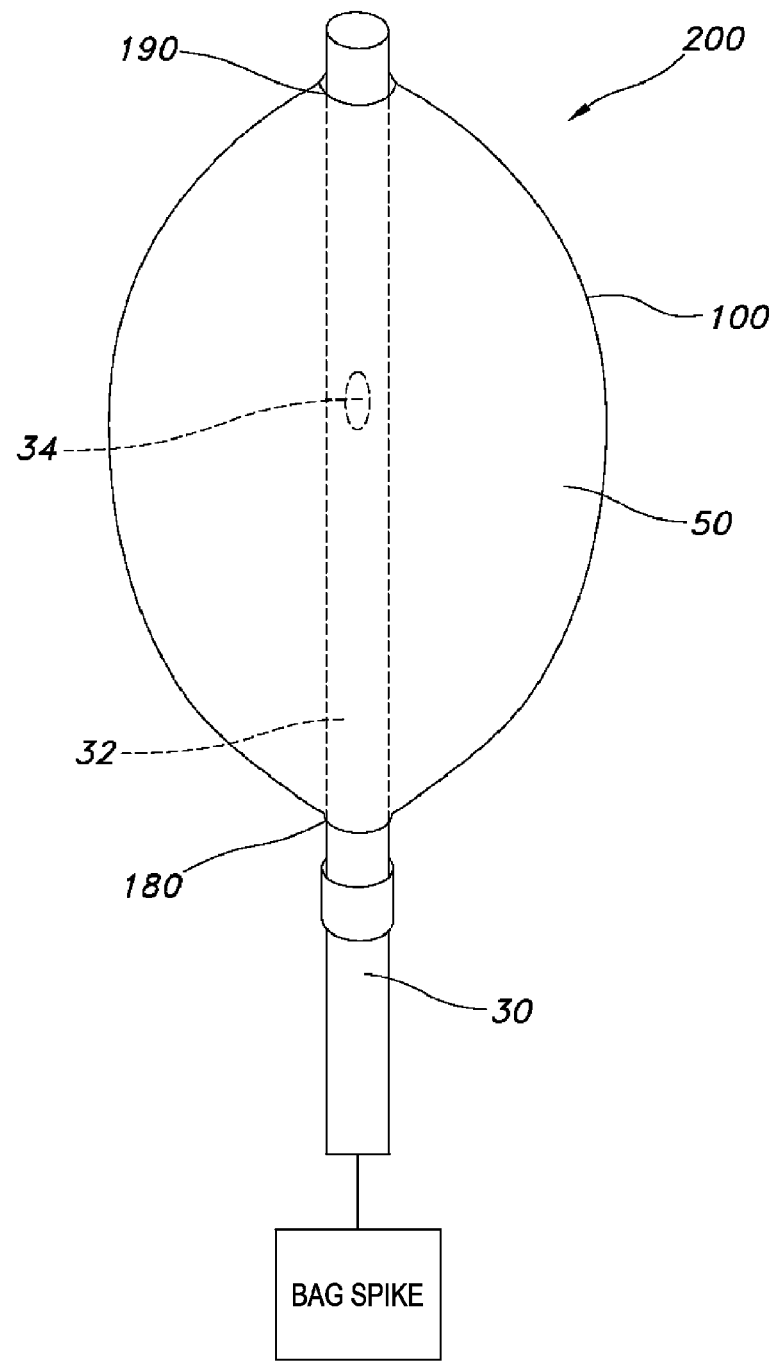
FIG. 1 illustrates a cross-sectional view of a non-inflated embodiment of a balloon tamponade of the invention.

Referring now to the drawings, wherein like numerals designate like and corresponding parts throughout the several views, in FIG. 1 is shown a balloon tamponade apparatus 200 for controlling hemorrhage in a pelvic or abdominal body cavity, comprising an expansible material (balloon) 100 having a distal end 190 (in reference to placement in the subject, a cephalic end) and a proximal end 180 (in reference to placement in the subject, a caudal end), and a conduit 30 having an inflation lumen 32 in communication with the interior 50 of the balloon through one or a plurality of openings 34. The inflation lumen provides a means to inflate or fill the balloon interior with a fluid medium (e.g., gas or liquid), thereby expanding the balloon to a shape within the body cavity. The inflation lumen also provides a means to deflate the balloon, by efflux or withdrawal of the inflation medium from the balloon, so that the apparatus may be removed from a body cavity of the subject. Preferably, at least a portion of the tube is sealably surrounded by the balloon, the seal proving a means to retain the inflation medium within the balloon interior and to secure the tube to the balloon.

The balloon is made of an expandable material, such as natural rubber, synthetic rubber, silicone, latex, urethane (polyurethane), polyvinylchloride, polyethylene, nylon or any other expansible elastomer, polymer or other material. Preferably, the balloon is formed of biocompatible, sterilizable material that is ultrasonic/radio opaque and may be treated with antimicrobial agents. Most preferably, the balloon will have sufficient compliance to generally conform to the shape, contours, walls and structures of a pelvic or abdominal cavity. However, it should be recognized by one in the art that in certain circumstances it may be preferable to have a balloon that is non-resilient and/or non-conforming and that will generally retain its original shape after inflation. In a preferred embodiment shown in FIG. 5 a vaginal balloon 150 having a cylindrical or oval shape will be non-conforming such that it retains the cylindrical or ovoid shape when inflated within a vagina.

Figure 2:
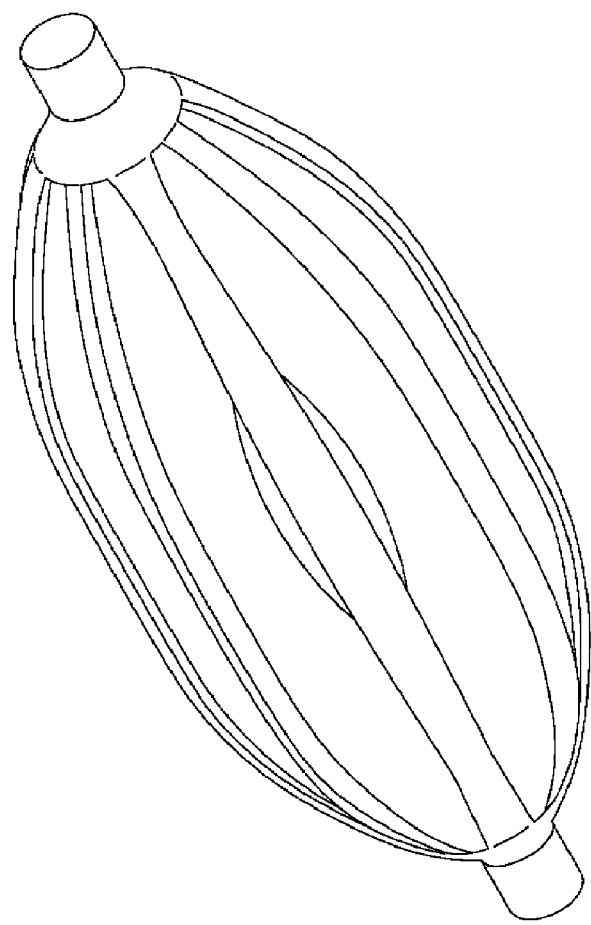
FIG. 2 illustrates an isometric elevation of a non-inflated, folded or pleated balloon of the invention.
Figure 3:
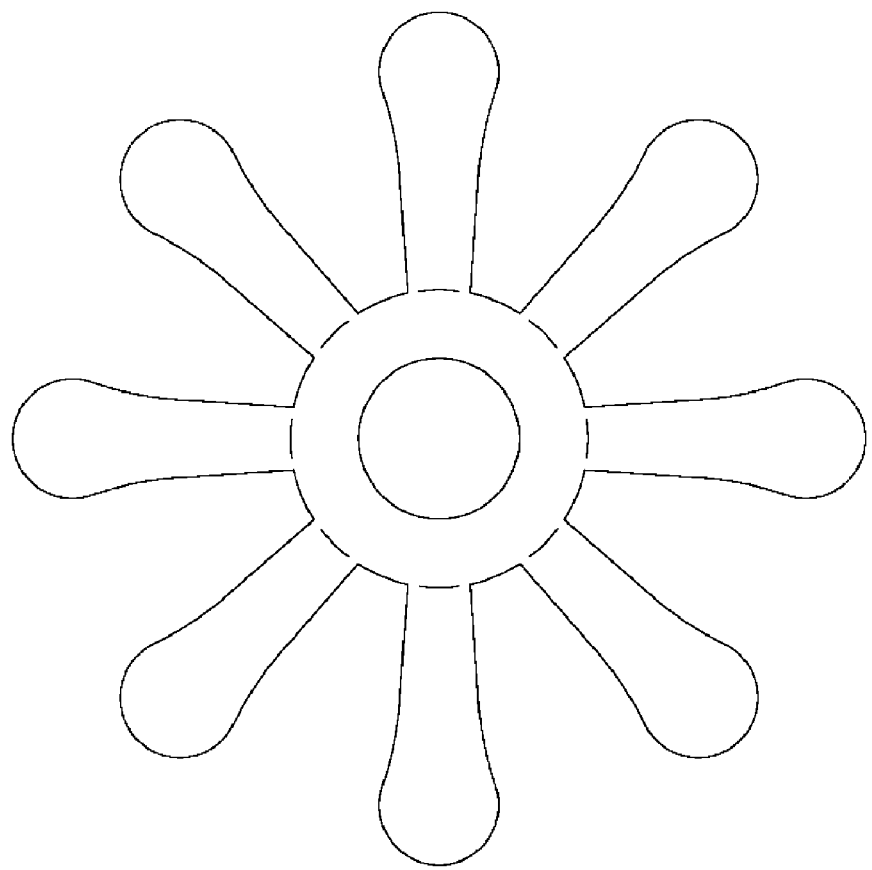
FIG. 3 illustrates a front elevation of a non-inflated, folded or pleated balloon of the invention.

The balloons of various embodiments of the invention may be of any shape, contour, size and volume. Preferably the shape, contour, size and volume are such that when inflated the balloon will generally conform to the body cavity where hemorrhage is to be controlled (i.e., the interior wall or surface or structure of the pelvis or abdominal cavity). Most preferably, the balloon will substantially conform to the body cavity. Conformance of the exterior shape of balloon with the interior wall, surface or structure of the body cavity enables the balloon to fit against a wall, surface, or structure thereby exerting a compressive force or pressure to control hemorrhage. The balloon may have folds, ribs, channels, undulations and/or other formations or contours to increase the expandable surface area of the balloon, or to facilitate expansion to a desired shape, or to facilitate conformance of the balloon with an interior surface, or to enhance balloon compliance to accommodate specific features, structures, tissues or organs of the body cavity. As shown in FIGS. 2 and 3, the balloon may comprise a plurality of fold or pleats to facilitate rapid fill or inflation to "fill volume" of the balloon, by overcoming the elasticity of the expansible material. Shapes particularly suited to the pelvic and abdominal cavities include spherical, mushroom, teardrop, heart or winged, ovoid, oblong and cylindrical. Balloons of the invention may be made by any conventional method known in the art, such as by extrusion or dip molding.

The balloon is constructed to be inflated by and hold a biologically and physiologically compatible medium, preferably a fluid and most preferably a liquid such as water or saline, or any other liquid used for intravenous infusion, such as Ringer's, lactated Ringer's, sterile water for injection, or sterile normal saline. The size and volume of the balloon will be determined by the body cavity or select area of a body cavity where hemorrhage control is desired. Balloons may be of any size or volume. Preferably balloon tamponades suitable for pelvic and abdominal cavities may be inflated or filled with fluid volumes between approximately 500 milliliters and approximately 5 liters, while balloon tamponades suitable for a uterine or vaginal cavity may be from approximately 200 milliliters to approximately 1 liter. If bleeding is known to originate from a particular area of a body cavity, a smaller size and volume balloon appropriate for the select area may be used to localize pressure to the select area of the body cavity. Also, male and female anatomy and subject size (e.g., adult vs. child) may dictate the shapes, contours, size and volume of the balloon that is suitable for control of hemorrhage from a body cavity of such a subject. For example, a balloon tamponade for a child may require a balloon volume capacity of approximately 500 milliliters to approximately 1 liter, while a balloon tamponade for large male adult may require a balloon of approximately 3.5 liters to approximately 5 liters.

In certain preferred embodiments, a balloon suitable for a pelvic or abdominal or uterine cavity may be of a size having 400 milliliters at neutral inflation (un-inflated), and 1 liter upon full fill volume when inflated. Most preferably, a balloon suitable for a pelvic or abdominal or uterine cavity may be of a size having 800 milliliters neutral inflation and 1.5 liters full fill volume when inflated. The deformation force (application of internal balloon traction means) should have no more than 10 N when inflated to full fill volume pressure, most preferably no more than 3 N when inflated to full fill volume pressure. Preferably, the diameter of the balloon before insertion (in the un-inflated state) will be no more than 3 centimeters, most preferably no more than 1 centimeter. The diameter of the balloon at deflation (removal diameter) is preferably no more than 4 centimeters, and most preferably no more than 2 centimeters. In certain preferred embodiments, a balloon suitable for a vaginal cavity may be of a size having a diameter of 10 centimeters and a length of twenty centimeters when fully inflated, preferably a diameter of 12 centimeters, and a length of 25 centimeters when fully inflated.

The tubes, tubing or conduits of the balloon tamponade apparatus and various aspects, features and embodiments of the invention, may be made of any biocompatible material, such as natural rubber, synthetic rubber, silicone, latex, urethane (polyurethane), polyvinylchloride, polyethylene (e.g., low density polyethylene), nylon, polycarbonate or any other biocompatible, flexible elastomer, polymer or other material suitable for tubes, conduits, tubing and catheters. However, it should be recognized by one in the art that in certain circumstances it may be preferable to have a conduit (or part of a conduit) that is less flexible or inflexible, rigid or semi-rigid (non-resilient and/or non-conforming), such as a portion of a conduit contained within a vaginal balloon. Preferably, the tube, conduit or tubing is formed of sterilizable material that is ultrasonic/radio opaque and may be treated with antimicrobial agents. Most preferably, the tube, conduit or tubing is made of polyethylene, silicone or nylon. As used herein, conduit may comprise a single tube having a single lumen, multiple tubes each having one or more lumens, a tube within a tube and each tubing having one or more lumens, or an extruded conduit having a plurality of lumens within the extruded conduit, in each instance having lumen diameters, lumen lengths and openings as suited to the particular purpose of the lumen. The "working length" of a lumen (i.e., the length needed to accomplish its function) may be changed by plugging or skiving the individual lumen to achieve desirable length to achieve or perform a particular function. For example, drainage and irrigation lumens will extend beyond the distal and proximal ends of the balloon, so that each such lumen may be in communication with a body cavity at or near the distal end of a balloon, and at the proximal end be in communication with the exterior of the subject's body. An inflation lumen may not extend the length of the balloon at the distal end, but may extend beyond the proximal end and have an opening in communication with the exterior of the subject's body for connection to a source of inflation media.

As more fully described below, the tube or conduit or tubing of various embodiments of the invention may comprise one or a plurality of lumens, the lumens having one or a plurality of openings for fluid communication with a balloon interior or a lumen or a separate tube or conduit or a body cavity. As shown in FIGS. 6a-g, lumens may be provided in any arrangement suitable for a particular embodiment of the invention described herein. FIGS. 6a and 6b illustrate a single tube having two lumens, FIGS. 6c and 6d illustrate a single tube having three lumens, FIGS. 6e and 6f illustrate a single tube having four lumens. The tubes and conduits of the balloon tamponade, and in particular those tubes and conduits that are physically contained within or surrounded by the balloon, are preferably sufficiently inflexible or rigid or inelastic to maintain their inner diameter when the balloon is inflated (e.g., made from a more rigid/inelastic material than the balloon or have a thicker cross-section than the wall of the balloon). The inflation lumen should be of a diameter sufficiently large to allow rapid inflation or filling of the balloon. Preferably the inflation lumen will be of a diameter to allow inflation or filling of the balloon in approximately three minutes or less, and most preferably in one minute or less. An inflation supply means may be provided inflate the balloon, such as a large syringe, a pump (e.g., an infusion pump), a filled IV fluid source (e.g. a bag or bottle) or other receptacle for holding a fluid, preferably a sterile sealed container readily available to medical personnel to contain or supply a physiological fluid.

Figure 4:
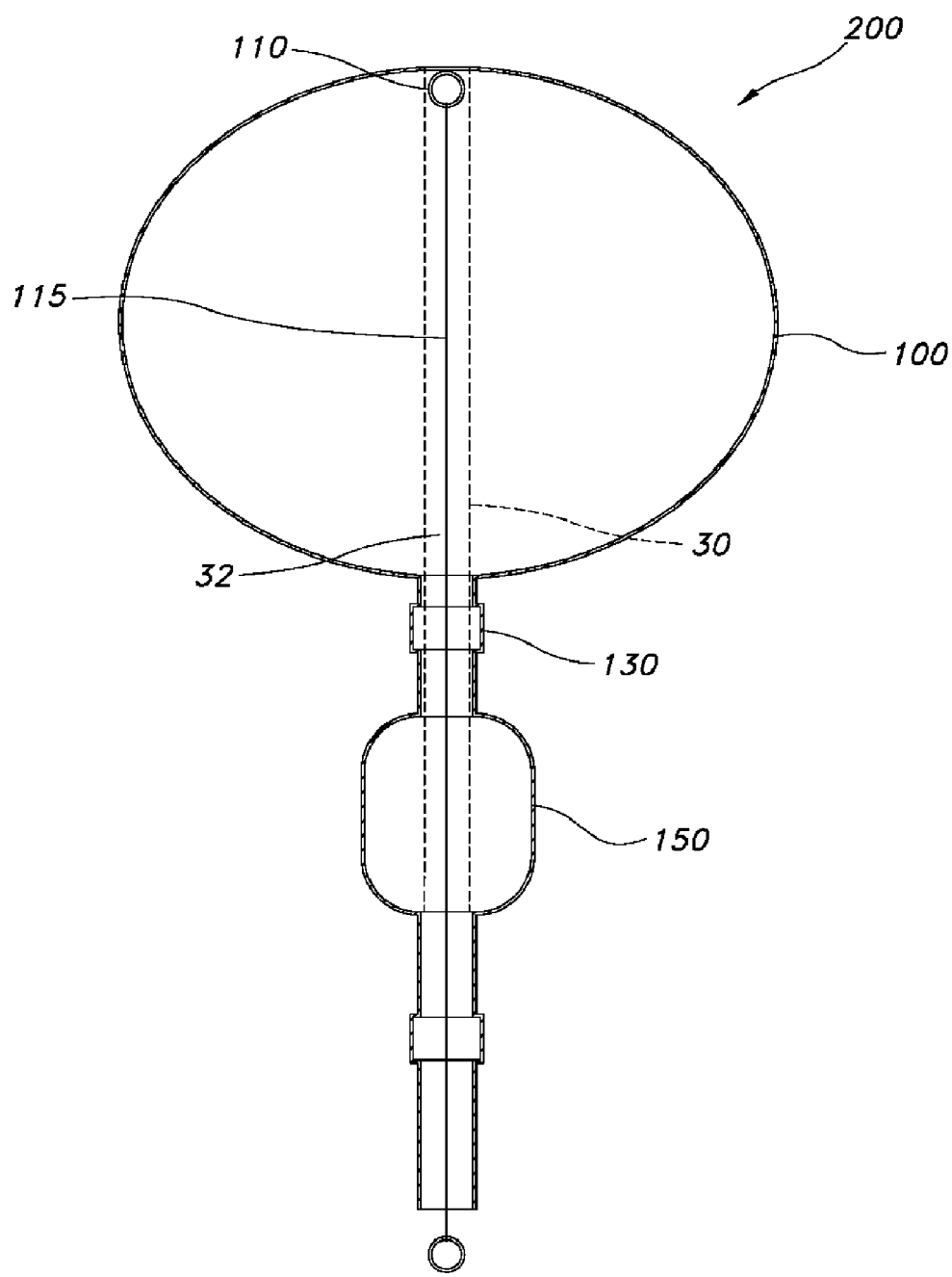
FIG. 4 illustrates a cross-sectional view of an inflated dual balloon tamponade of the invention.

As show in FIG. 4, in another aspect, the invention provides a deforming means for deforming the shape of the balloon or limiting expansion of the balloon in a first direction, so that when the balloon is inflated more force is exerted in a second direction against a wall or surface or structure (e.g., a bone, a blood vessel, an organ or a tissue) within the body cavity to control hemorrhage. The deforming means may be any suitable means to limit expansion of an expansible material or to exert a deforming, resistive or opposing force to expansion of a wall of the balloon during inflation of the balloon or to change the dimension of a balloon or change the shape of a balloon. For example, in a preferred embodiment, as shown in FIG. 4, traction means 115 (e.g. a wire, cable, filament, or other tensile attachment) is attached by a traction connecting means (e.g., a loop, an adhesive, a fitting, etc.) 110 to a wall at the distal end 190 of the balloon and extends the length of the balloon to a traction application means 120, such as a tab, a grip, a ring, a ratchet, a clamp, a friction wheel, a bead or step catch, or other latching or locking means or other means to apply a traction force to the traction means. Placing a traction force (e.g., pulling downwardly) on the traction application means during inflation (or after inflation) will deform the expansible shape of the balloon, limit upward expansion of the balloon and cause the balloon to expand more laterally, thereby selectively causing pressure laterally and downwardly along the sides and base of the body cavity. Alternatively, a traction wire, cable, filament or other tensile or tensioning means may be attached (fixedly or releasably) to a portion of the conduit 30 or to an internal cuff 130 surrounding the conduit at or near the proximal (caudal) end of the balloon, which provides a traction force during inflation to deform the shape of the balloon or limit upward expansion of the dome (distal/cephalic end) of the balloon. Alternatively, the deforming means may be an area or wall of expansible material having less expansibility or elasticity than another area or wall of the balloon, thereby deforming the balloon shape or limiting the expansion of the balloon in that area. For example, the deforming means may be a cap or disk within a wall of the balloon, or a collar (rigid or semi-rigid) disposed over a wall or area of the balloon. In yet another embodiment, the deforming means may be a second balloon that, when inflated or filled, provides a resistive force against expansion of the first balloon.

In yet another embodiment, the traction means may be the cuff of the balloon disposed (rolled) inside the balloon during assembly to effectively position the cuff approximately medial to portion of the conduit surrounded by the balloon interior, wherein the conduit provided thereby becomes a traction means. When tension is applied to the conduit, the proximal end of the balloon "roll ups" over the cuff, deforming the balloon's shape to more elliptical in the lateral or horizontal axis than in the longitudinal axis, and forcing the proximal end of the balloon to conform to the surrounding anatomy of the body cavity.

In yet another embodiment, a balloon may be formed of an expansible material that increases in thickness in an area of the wall of the balloon, thereby limiting the expansibility of the balloon at the thicker wall, deforming the shape of the balloon and causing expansion of the balloon to be directed in areas where the balloon wall is of lesser thickness or greater expansibility. Most preferably, the thickened area is at the distal or cephalic end of the balloon so that expansion is limited at the cephalic end or in the cephalic-caudal axis, thereby facilitating expansion of the balloon laterally (dorsal axis) and in the anterior (front) and posterior (back) axis.

Figure 5:
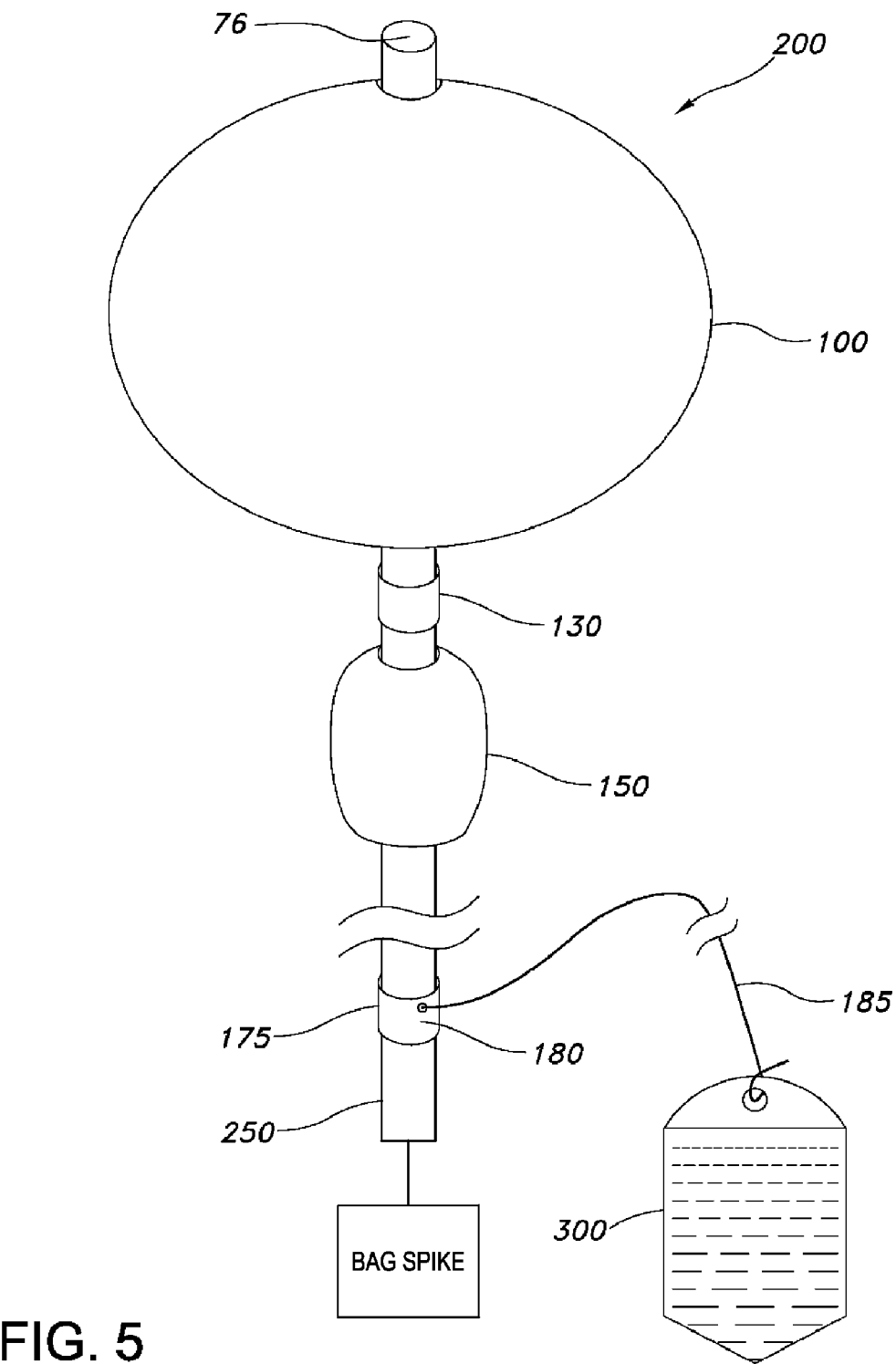
FIG. 5 illustrates an elevation of an inflated dual balloon tamponade of the invention.

As shown in FIGS. 5 and 6, in yet another embodiment of the invention, the balloon tamponade apparatus comprises an expansible balloon and a conduit, a conduit 30 comprising an inflation lumen 32 in communication with the interior of the balloon and a drainage/irrigation lumen 70 that extends beyond the distal (cephalic) end of the balloon and having a distal opening 72 in communication with a pelvic or abdominal cavity and a proximal opening 76 in communication with the exterior of the subject's body. Preferably, the distal and proximal openings are located at or near opposing ends of the drainage/irrigation lumen. The drainage/irrigation lumen provides a means to drain the body cavity (e.g., of blood, debris, and irrigation fluids) and to irrigate the body cavity with cleansing and hydrating fluids (e.g., water or saline) and therapeutic agents (e.g., pharmaceuticals) or diagnostic instruments. In an alternate embodiment as shown in FIGS. 6c-g, the balloon tamponade apparatus provides separate irrigation 72 and drainage 74 lumens to minimize contamination of the body cavity (e.g., due to return of debris to the body cavity during supply of irrigation fluid). Preferably, the proximal end of the conduit comprising the drainage/irrigation lumen (whether a single lumen or separate lumens) extends outside the body to facilitate irrigation and collection of drainage materials. Preferably, the drainage lumen has a diameter sufficient to permit removal (by flushing or suction) of debris (pieces of tissue, cells, blood clots) that may enter the drainage tube, and to prevent such debris from blocking drainage of fluids through the drainage lumen.

In a preferred embodiment, as shown in FIG. 5, the balloon tamponade comprises a conduit assembly having a distal end and a proximal end, a first balloon 100 and a second balloon 150 co-axially spaced along the conduit, wherein the conduit is sealably surrounded by each of the first balloon and the second balloon and comprises a first inflation lumen (40 as shown in FIG. 6g), in communication with the interior of the first balloon interior and a second inflation lumen (42 as shown in FIG. 6g) in communication with the interior of the second balloon. The first balloon has at least a fold or pleat to facilitate rapid fill and inflation and is axially spaced along the conduit adjacent to the distal end of the conduit. The second balloon is of a cylindrical shape and is non-conforming to substantially retain the cylindrical shape upon inflation. In the conduit assembly, the second conduit is slideably disposed over the first conduit and the conduit assembly comprises the lumen configuration shown in FIG. 6g. The second conduit has a joint disposed between the first and second balloons, wherein the joint is comprised of a joint fitting to allow the second balloon to be disjoined from the first balloon at the joint. The joint fitting may be a friction bit, a snap fitting, a threaded fitting, a taper-fit, a collar, a bayonet fitting, or a quick-release fitting.

In still other embodiments, the balloon apparatus may further comprise one or more connecting means to connect a lumen of conduit to a lumen of a tube or to a medium source (e.g., irrigation fluid or inflation media), or to a drainage receptacle, or to a control means or pressure detection means (as described below) that is located external to the body. Any conventional connecting means may be employed, such as luers/leurs, lugs, locks, lock nuts, rings, fittings, Y connectors, adapters, connecting means described in U.S. Pat. No. 6,520,977 (which is incorporated herein), and any other means suitable for connecting tubes, conduits, tubing, or control means. Connecting means for use in medical applications are commercially available and well known in the art. Preferably, where an IV bag is the inflation supply source, the connecting means for connecting an inflation lumen to inflation supply source is a bag spike to puncture an IV bag to facilitate rapid fill of the balloon.

In yet other embodiments, a control means is provided to seal or unseal, or retain or release, or regulate flow of fluids through, the lumens of the tubes, conduits and tubing of the invention. The control means may be any means suitable for sealing and unsealing, or regulating flow through a lumen, or to control influx or efflux through the lumen or to retain or release a fluid within a lumen. Control means may include volume flow regulators, valves (e.g., ball valves or needle valves), stop-cocks, clasps, clamps (e.g., pinch, spike, slide and roller clamps), clips, caps, plugs, stoppers and any other means suitable for sealing or unsealing a tube or conduit or tubing. Such control means for use in medical applications are commercially available and well known in the art. Preferably, control means for irrigation tubes or lumens have a means to provide flow in one direction (e.g., one-way valves) to prevent reverse flow. Control means for the deflation lumen or drainage lumen preferably comprise a one-way stop-cock.

In yet other embodiments, the balloon tamponade may further comprise a means to detect the level of pressure within the balloon interior, such as a simple pressure gauge. The pressure detection means may be connected by connecting means to the inflation lumen. During inflation of the balloon, the pressure gauge needle will pulse in concert with the subject's heart beat. When the balloon is inflated with sufficient pressure (i.e., at or just above the blood pressure of the subject), the pressure gauge needle will cease pulsing.

In yet other embodiments, as shown in FIG. 5 the balloon tamponade apparatus may further comprise an external traction connecting means 175 for attachment of an external traction source 300 to apply external traction to the balloon tamponade apparatus after inflation has been completed. External traction source 300 may be any means to apply a traction force in the caudal direction, such as by manually pulling, attaching a weight or a filled IV bag/bottle or by taping a traction line to a subject's leg. External traction to the balloon tamponade provides yet another means to apply compressive force in the caudal direction toward the base of the body cavity. The external traction source 300 is attached to external traction connecting means 175 (fixedly or releasably) by an attachment means 185, such as a wire, filament or string. Preferably, the external traction connecting means 175 comprises a semi-rigid cuff or rigid cuff having a fastening means for fastening an external traction attachment means to the cuff. The cuff may be sealably or removably attached to a conduit of the balloon tamponade preferably at or adjacent to the proximal end of the conduit.

In certain embodiments of the balloon tamponade, the apparatus may further comprise an introducer assembly for aiding insertion of the balloon tamponade apparatus into a pelvic or abdominal cavity from an opening in the body (for example, in a hysterectomy patient through the vagina, or in a male patient through an incision the perineum). The introducer assembly is generally used to prevent the balloon tamponade device from flexing excessively during insertion. The introducer assembly comprises a wire attached to a gripping means at a proximal end. The wire is threaded from the proximal end to the distal end of a lumen of the conduit and extends substantially the length of the balloon. Preferably, the introducer wire is threaded through a lumen that is not in communication with a body cavity (e.g., not threaded through an irrigation lumen or drainage lumen). Preferably the wire of the introducer assembly extends to within one or two centimeters from the distal end of the lumen. Generally, the introducer assembly is removed from the lumen of the balloon tamponade after balloon tamponade insertion and placement in the body cavity has been accomplished. The wire may comprise a trocar, guide, stem, stylet or other semi-rigid or rigid means to aid insertion of a tubular medical device (e.g., a catheter,) into a subject. The traction wire describe above may also function as an introducer in certain embodiments of the invention. In an alternate embodiment, the introducer may be surrounded by a drain tube or an irrigation tube. The insertion means may be hollow or solid and may be made of any suitable material that will not damage the balloon or the body cavity, or the organs or tissues of the subject, such as natural or synthetic rubber, latex, semi-rigid polymers (e.g., polyethylene or polyvinyl chloride or polycarbonate), or of metal.

In other embodiments, an external surface of the balloon may be coated (e.g., by layer, film, spray, gel or powder), impregnated, infused, permeated or otherwise comprise a hemostatic material or a pharmaceutical composition in order that the hemostatic material or composition may come into general contact with a wall, tissue, or structure within a body cavity. Any pharmaceutical may be used, and hemostatic agents such as oxidized cellulose, hemotene, thrombin, Factor VII, and other blood clotting factors are particularly suitable for use in connection with the balloon tamponade.

In a preferred embodiment shown in FIG. 5, the balloon tamponade apparatus comprises a first balloon having a distal end and proximal end, sealably surrounding a portion of a first conduit having a first lumen and in communication with the interior of the first balloon. At the proximal end of the balloon, the balloon meets an external portion of the first tube at an internal cuff 130. The first conduit extends to the exterior of the body 250 and is connected to a control means for maintaining the balloon in an inflated state and for controllably releasing fluid from (deflating) the balloon when pressure to the body cavity is to be reduced or when the device is to be removed from the body cavity.

In a preferred embodiment, there is provided a balloon tamponade for controlling hemorrhage in a body cavity of a subject, comprising an expansible balloon comprising a plurality of folds or pleats, and having a distal end and a proximal end. The device further comprises a conduit sealably surrounded by the balloon, having a distal end and a proximal end and having an inflation lumen, a guide lumen, an irrigation lumen and a drainage lumen. A traction means (preferably a wire or cable) extends the length of the guide lumen. A traction connecting means, preferably a cuff, is disposed along the conduit at or near the proximal end of the conduit. The inflation lumen is in communication with the interior of the balloon and the guide lumen is in communication with an interior surface at the distal end of the balloon. The irrigation lumen and drainage lumen are each in communication with a body cavity through openings at or near the distal end of the conduit and are each in communication with the exterior of the subject's body through opening at or near the proximal end of the conduit. The traction means is attached to an interior surface of the balloon at the distal end of the balloon and is attached to traction connecting means (e.g., cuff) at the proximal end of the conduit.

In yet another embodiment, a dual balloon tamponade for controlling hemorrhage in a body cavity comprises a first balloon and a second balloon each having a distal end and a proximal end. The first balloon comprises a plurality of folds or pleats. A first conduit, having a distal end and a proximal end, comprises a first inflation lumen in communication with the interior of the first balloon, and is sealably surrounded by the first balloon. A second conduit has a distal and proximal end and comprises a second inflation lumen in communication with the interior of the second balloon. The second conduit is sealably surrounded by the second balloon and the second conduit is slidably arranged over the first conduit. A first semi-rigid cuff disposed between the first and second balloons, surrounds either the proximal end of the first balloon or the distal end of the second conduit. In other embodiments, the first conduit further comprises an irrigation lumen and a drainage lumen, each of the irrigation lumen and drainage lumen having an opening in communication with a body cavity and an opening in communication with the exterior of the subject's body, to provide channels for irrigation of and drainage from the body cavity. Fitting means may be provided for releasably fitting the second conduit to the first conduit. Such fitting means may include a friction bit, a snap fitting, a threaded fitting, a taper-fit, a collar, a bayonet fitting, or a quick-release fitting.

FIG. 6a illustrates yet another embodiment, in which the inflation lumen may comprise a bifurcated lumen 32a and 32b, and each one of such bifurcated lumens may be attached to a control means, thereby allowing simultaneous infusion/ inflation to and drainage of a physiological medium from the balloon interior, or allowing the physiological medium within the balloon to be exchanged as needed (e.g., allow for fluid replacement) without altering the pressure within the balloon. The bifurcation of the inflation lumen also permits substantially continuous circulation of a physiological medium into and out of the balloon, such as when heating or cooling of the body cavity is desired. In a preferred embodiment, an additional tube provides an inflow and outflow means for a physiological medium capable of being heated or cooled, thus providing a means to heat or cool the physiological medium within the balloon interior where said tube may constitute one or more lumens in an open or closed-loop configuration, with or without exchange external to the tube. Specifically, a loop may be created of a tube such that the diameter is compatible with existing peristaltic or infusion or other pumps and heat or cooling sources, so that the fluid within the balloon(s) may be circulated in a closed loop by the pump through a heat or cooling source in order to increase or decrease body cavity temperature.

In yet another aspect, the invention provides a rapid-fill balloon for controlling hemorrhage in a body cavity, comprising an expansible balloon having a plurality of folds or pleats. The balloon has a fluid fill volume (volume upon full inflation) of between 300 and 1000 milliliters, and is capable of being inflated to fill volume in less than three minutes without requiring application of pressure to overcome the elasticity of the balloon.

In yet another aspect of the invention, there is provided a kit for controlling hemorrhage in a pelvic or abdominal cavity, comprising an embodiment of the expansible balloon tamponade apparatus described herein, and instructions for use of such material, and packaging for containing the balloon tamponade apparatus and instructions. In another, preferred embodiment, the balloon tamponade kit further comprises a drainage receptacle and a connecting means to releasably connect the drainage lumen to the drainage receptacle to collect fluid and debris that is discharged from the drainage lumen. In still other embodiments, the kit may further comprise inflation supply tubing and/or irrigation supply tubing and/or drainage efflux tubing, or any combination thereof, together with connecting means suitable for connecting such inflation supply, irrigation supply or drainage efflux tubing to the balloon tamponade apparatus. In certain preferred embodiments, the kit may further comprise a pharmaceutical agent, such as a hemostatic agent that may be applied to the surface of the balloon before implantation. The kit may further comprise digital or electronic information and instructions on use, insertion and implantation of the balloon tamponade devices, such as a video cassette, compact disk (CD), digital video disk (DVD), flash or zip or thumb drive, or any other means to electronically store information that may be accessible by a computer.

Another aspect of the invention provides a method to control hemorrhage in a body cavity, by providing a balloon tamponade in an unfilled (non-inflated) state, implanting or inserting the balloon tamponade into a body cavity (with or without the assistance of an introducer), filling the balloon with a biologically and physiologically compatible fluid through the inflation lumen of the tube (preferably a warmed or cooled sterile fluid) supplied from an external inflation media supply source, such as a filled IV bag or a syringe filled with the inflation medium. The physiologic medium is supplied at a pressure and volume sufficient to inflate the balloon (or the particular balloon of a dual balloon tamponade, as applicable). During the infusion of the physiologic medium, the balloon distends and its effect on bleeding is observed by efflux from a drain tube. Preferably, the effluent is collected for measurement and evaluation. The preferred inflation pressure of the balloon is the lowest pressure which controls bleeding from the particular body cavity in which it is placed, and most preferably the pressure which staunches bleeding from the body cavity of the subject.

When the desired volume or pressure is reached in the balloon interior, a control means may be manipulated to cease further infusion of the inflation medium and/or to retain the inflation medium in the balloon interior and the inflation lumen. The external source of the medium is disconnected, and a drainage bag or other drainage collection receptacle may be releasably attached by connecting means to the drainage lumen (or to a drainage efflux tubing connected to the drainage tube through a connecting means) to capture drainage fluid. Optimum pressure is detected, for example, when there is no further fluid drainage from the drain tube or when blood clots are observed in the drain tube, indicating that normal coagulation has been restored in the subject. After an appropriate length of time, balloon pressure may be lowered (fluid gradually drained or released from the balloon through the inflation or deflation lumen, as applicable) and observations made to determine whether or not bleeding has been controlled (i.e., whether bleeding is observed in the drain tube). If bleeding is observed upon release of balloon pressure, then the balloon may be re-inflated to an appropriate pressure to control hemorrhage.

These and other aspects, features and advantages of the present invention are apparent from the detailed description when taken in conjunction with the drawings. In addition to the objects, features and advantages in the embodiments and examples described above, other objects, features and advantages of the present invention will be apparent to those skilled in the art. The disclosed aspects are merely illustrative of the innumerable aspects associated with the present invention and should not be deemed as limiting in any manner. Although methods and materials similar or equivalent to those described herein may be used in the practice of the present invention, suitable methods and materials are described above. The materials, methods and examples are illustrative only and not intended to be limiting in any manner. While preferred examples and steps of the present invention have been illustrated and described, this has been by way of illustration and the invention should not be limited except as required by the scope of the appended claims and their equivalents.

What is claimed is:

1. An apparatus for controlling gynecologic and obstetric hemorrhage in a body cavity of a subject, comprising:
   at least one expandable balloon having a distal end and a proximal end, the at least one expandable balloon has a flexible structure adapted to be inserted into the uterine cavity and can be filled with fluid volumes between 200 milliliters and 1.0 liter, wherein the exterior shape of the balloon conforms to the area within the uterine cavity;
   a conduit extending from a proximal end portion of the apparatus to a distal end portion of the apparatus, the conduit sealably surrounded, in part, by the at least one expandable balloon and including at least one inflation lumen in communication with the interior of the at least one expandable balloon; and
   a fluid supply fitting disposed at the proximal end portion of the conduit, the fluid supply fitting configured to directly connect a liquid supply bag to the at least one inflation lumen and facilitating inflation of the at least one expandable balloon to an expanded liquid fill volume in three minutes or less.

2. The apparatus of claim 1, comprising an internal cuff surrounding a portion of the conduit and co-axially spaced on the conduit apart from the at least one expandable balloon, wherein the at least one expandable balloon is configured to deform in shape by inhibiting expansion in at least a first direction and facilitating expansion in at least a second direction, different from the first direction, using the internal cuff.

3. The apparatus of claim 1, wherein the conduit includes at least a second lumen in addition to the at least one inflation lumen, the second lumen and the at least one inflation lumen separated by a plurality of tubes within, or internal webbing of, the conduit.

4. The apparatus of claim 3, wherein at least the second lumen is configured to allow for one or both of drainage from, or irrigation to, the body cavity when the at least one expandable balloon is implanted, the second lumen including an opening at or near the distal end of the conduit for communication with the body cavity and an opening at or near the proximal end of the conduit for communication with an exterior of the subject's body.

5. The apparatus of claim 1, comprising a traction means configured to prevent upward displacement of the apparatus further into the body cavity, when implanted in the body cavity.

6. The apparatus of claim 1, wherein the at least one expandable balloon comprises a first expandable balloon and a second expandable balloon co-axially spaced on the conduit from one another, wherein the conduit comprises a first conduit and a second conduit, the first conduit is sealably surrounded, in part, by the first expandable balloon and includes a first inflation lumen in communication with the interior of the first expandable balloon, and the second conduit is sealably surrounded, in part, by the second expandable balloon and includes a second inflation lumen in communication with the interior of the second expandable balloon.

7. The apparatus of claim 6, wherein the first expandable balloon includes at least one fold or pleat configured to facilitate inflation of the balloon.

8. The apparatus of claim 6, wherein the first expandable balloon is positioned distal of the second expandable balloon and includes a liquid fill volume greater than the second expandable balloon.

9. The apparatus of claim 6, wherein the second expandable balloon includes a shape having a maximum diameter between approximately 10 centimeters and approximately 12 centimeters upon inflation.

10. The apparatus of claim 6, wherein a connection disposed between the first and second expandable balloons includes a fitting, the fitting configured to allow the second expandable balloon to be disjoined from the first expandable balloon.

11. The apparatus of claim 6, wherein one or both of the first or second expandable balloons are inflatable to the expanded liquid fill volume in about one minute or less and include a urethane material.

12. The apparatus of claim 1, wherein the at least one expandable balloon has a fluid fill volume between 300 milliliters and 1.0 liters and is capable of being inflated to fill volume in less than three minutes without requiring application of pressure to overcome the elasticity of the balloon.

13. The apparatus of claim 5, wherein the traction means is selected from a group consisting of a tab, a ring, a grip, a ratchet, a clamp, a friction wheel, a bead or step catch, or other latching or locking means at an internal cuff or an external cuff.

14. The apparatus of claim 3, wherein at least the second lumen comprises a deflation lumen in communication with the at least one expandable balloon interior, the at least one inflation lumen and the deflation lumen configured to allow substantially simultaneous liquid supply and liquid withdrawal from the interior of the at least one expandable balloon to replace or circulate an inflation liquid therethrough.

15. The apparatus of claim 14, wherein the inflation liquid is warmed or cooled in order to warm or cool the body cavity.

16. The apparatus of claim 14, wherein liquid circulation for warming or cooling is enabled by a closed loop which connects the inflation and deflation lumens.

17. The apparatus of claim 1, comprising a connecting means connected to the proximal end of the inflation lumen of the conduit.

18. The apparatus of claim 1, comprising a pressure gauge or sensor configured to detect the internal pressure of an inflation liquid within the at least one expandable balloon.

19. The apparatus of claim 17, wherein the connecting means comprises a luer lock.

20. The apparatus of claim 1, comprising a control means connected to a drainage lumen of the conduit to control drainage from the body cavity, wherein the control means is a stop-cock.

21. The apparatus of claim 1, wherein the at least one expandable balloon is of a size having 800 milliliters neutral inflation and 1.5 liters full fill volume when inflated.

22. The apparatus of claim 1, wherein an external surface of the at least one expandable balloon is coated, impregnated, infused, permeated or otherwise includes one or both of a hemostatic material or a pharmaceutical composition for contact with a wall, tissue or structure within the body cavity, when implanted.

23. The apparatus of claim 2, wherein the at least one expandable balloon is configured such that placement of a force, in a direction toward an end of the apparatus, on the conduit portion limits expansion of the balloon in the first direction and facilitates expansion, at least partially, in the second direction.

24. A balloon tamponade for controlling gynecologic and obstetric hemorrhage in a body cavity of a subject, comprising:
   an expansible balloon having a distal end and a proximal end which has a flexible structure adapted to be inserted into the uterine cavity and can be filled with fluid volumes between 300 milliliters and 1,000 milliliters in three minutes or less to substantially fill a first body cavity;
   a conduit having a distal end and a proximal end and having an inflation lumen, a guide lumen, an irrigation lumen and a drainage lumen;
   a traction wire extending the length of the guide lumen; and
   an internal cuff surrounding the conduit at or near the proximal end of the balloon, wherein the conduit is sealably surrounded, in part, by the balloon, the inflation lumen is in communication with the interior of the balloon and the guide lumen is in communication with an interior surface of the balloon at the distal end of the balloon, and wherein the irrigation lumen and drainage lumen are each in communication with the body cavity through openings at or near the distal end of the conduit and are each in communication with the exterior of the subject's body through an opening at or near the proximal end of the conduit, and wherein the traction wire is fixedly attached to the interior surface of the balloon at the distal end of the balloon and is fixedly attached to the internal cuff at the proximal end of the balloon.

25. A dual balloon tamponade for controlling gynecologic and obstetric hemorrhage in a body cavity of a subject, comprising:
- an expandable first balloon having a distal end and a proximal end which has a flexible structure adapted to be inserted into the uterine cavity and can be filled with fluid volumes between 300 milliliters and 1,000 milliliters in three minutes or less to substantially fill a first body cavity;
- an expandable second balloon configured to substantially fill a second body cavity, the second balloon co-axially spaced from the first balloon, having a distal end and a proximal end;
- a first conduit having a distal end and a proximal end, and comprising a first inflation lumen in communication with the interior of the first balloon and being sealably surrounded by the first balloon; and
- a second conduit having a distal and a proximal end, and comprising a second inflation lumen in communication with the interior of the second balloon and being sealably surrounded by the second balloon, and wherein the second conduit is slidably engaged over the first conduit.

26. The apparatus of claim 25, comprising a fluid supply fitting disposed at or near the proximal end of the first or second conduit, the fluid supply fitting configured to directly connect a liquid supply bag to the first or the second inflation lumen thereby facilitating rapid inflation of the expandable first balloon or the expandable second balloon when pressure is applied to the liquid supply bag.

27. The dual balloon tamponade of claim 25, wherein the second conduit has a joint disposed between the first and second balloons, wherein the joint is comprised of a joint fitting to allow the second balloon to be disjoined from the first balloon.

28. The dual balloon tamponade of claim 25, wherein the balloons are inflated by filling with a volume of liquid via an IV bag, wherein the IV bag is spiked and squeezed through a direct fill mechanism.

29. The dual balloon tamponade of claim 25, wherein the first balloon is conforming and the second balloon is nonconforming to the area within the uterine cavity.

30. The dual balloon tamponade of claim 25, wherein the first balloon is made of polyurethane.

* * * * *